United States Patent [19]

Wong

[11] Patent Number: 5,017,501

[45] Date of Patent: May 21, 1991

[54] PREPARATION OF UNIFORMLY SIZED LIPOSOMES ENCAPSULATING AN AQUEOUS LIQUID

[75] Inventor: Martin Wong, Grayslake, Ill.

[73] Assignee: Abbott Laboratories, Abbott Park, Ill.

[21] Appl. No.: 300,002

[22] Filed: Jan. 19, 1989

Related U.S. Application Data

[62] Division of Ser. No. 125,505, Nov. 25, 1987, Pat. No. 4,873,035.

[51] Int. Cl.$^5$ .................. G01N 33/544; B01J 13/02; A61K 37/22; C12N 11/02
[52] U.S. Cl. .................................. 436/528; 264/4.1; 424/450; 435/177; 435/182; 436/829
[58] Field of Search .................. 435/174, 177, 182; 436/528, 829; 424/450; 264/4.6, 4.1

[56] References Cited

U.S. PATENT DOCUMENTS

| | | | |
|---|---|---|---|
| 3,887,698 | 6/1975 | McConneil et al. | 435/7 |
| 4,224,179 | 9/1980 | Schneider | 252/316 |
| 4,342,826 | 8/1982 | Cole | 435/177 X |
| 4,485,054 | 11/1984 | Mezei et al. | 264/4.6 |

FOREIGN PATENT DOCUMENTS

| | | |
|---|---|---|
| 0119020 | 9/1984 | European Pat. Off. |
| 0186352 | 7/1986 | European Pat. Off. |

OTHER PUBLICATIONS

Bangham, A. D., et al., *J. Mol. Biol.*, 13:238–252 (1965).
Deamer, D. W. and Uster, P. S., "Liposomes", Ch. 1, Liposome Preparation: Methods and Mechanisms; and Marc J. Ostro (ed.), M. Dekker, Inc., pp. 27–51, New York, NY (1983).
Juliano, R. L. and Stamp, D., *Bioch. Biophys. Res. Communications*, 63:651–658 (1975).
Papahadjopoulos, D. and Miller, N., *Biochimica et Biophysica Acta*, 135:624–638 (1967).
Richards, R. L., et al., *Biochimica et Biophysica Acta*, 855:223–230 (1986).
Scherphof, G. L., et al., *Biochemical Society Transactions*, 15:345–348 (1987).
Scherphof, G. L., et al., *Liposome Technology*, vol. III, pp. 205–224, Edited by G. Gregnodia, CRC Press Boca Raton, Fla. (1984).
Szoka, F., *Ann. Rev. Biophys. Bioeng.*, 9:467–508 (1980).
Szoka, F., et al., *Proc. Nat'l. Acad. Sci.* (USA), 75:4194–4198 (1978).
Wong, M., et al., *Biochemistry*, 21:4133–4139 (1982).

*Primary Examiner*—David M. Naff
*Attorney, Agent, or Firm*—Daniel W. Collins; Roberta L. Hastreiter

[57] ABSTRACT

A dispersion of a uniformly sized population of multilamellar lipid vesicles (liposomes) encapsulating an aqueous liquid is prepared by forming a dried film of lipids on the walls of a vessel, contacting the film with an aqueous liquid in the presence of spherical contact masses such as glass beads and agitating. The liposomes have mean diameters in the range of about 150 to about 3000 nanometers and the contact masses have mean diameters of about 50 to 3,000 microns. The aqueous liquid encapsulated may contain enzymes, drugs or marker substances such as colorimetric or fluorescent dyes. A member of a immunological binding pair may be associated with the surfaces of the liposomes for carrying out immunoassays. This method allows for the use of small quantities of marker and lipid, leaves no residual solvents, allows for contact with only glass surfaces and involves no transfer of liposome preparations from lipid film drying vessels to sizing apparatus.

3 Claims, 1 Drawing Sheet

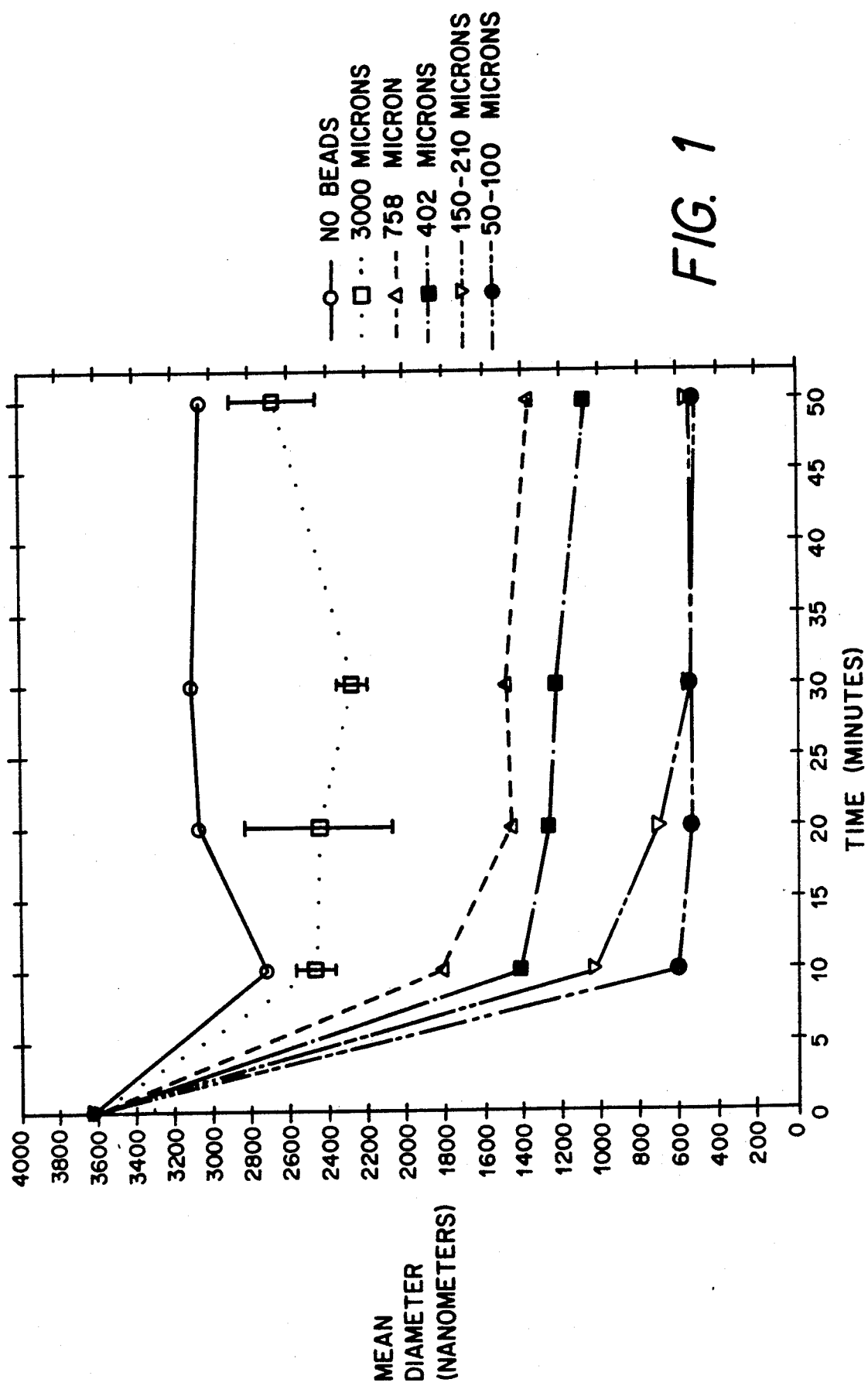

PREPARATION OF UNIFORMLY SIZED LIPOSOMES ENCAPSULATING AN AQUEOUS LIQUID

This is a division of application Ser. No. 125,505, filed Nov. 25, 1987, now U.S. Pat. No. 4,813,035.

BACKGROUND OF THE INVENTION

The present invention relates generally to a method for the preparation of uniformly sized populations of lipid vesicles, liposomes, which may be used to encapsulate aqueous materials.

Liposomes are spherical shells of amphipathic molecules which isolate an interior aqueous space from the bulk exterior aqueous environment and are characterized by their lipid composition, the most commonly used lipid component being phospholipid. Because liposomes can be made to contain hydrophobic molecules within their membrane, or hydrophilic markers within their internal aqueous space, or both, liposomes are used as potential vehicles for the delivery of drugs in vivo and as the basis for immunoassay systems in vitro such as the Liposome Immuno-Lytic Assay (LILA) which involves the antibody-triggered complement-mediated lysis of liposomes. For use in such complement-mediated immunoassays, liposomes should be homogeneous in size distribution, be small enough to remain in suspension, and be large enough to entrap sufficient marker, such as fluorophore or enzyme; to provide a high signal.

Many methods have been described in the literature for making a wide variety of both multilamellar and unilamellar liposomes. See, Szoka, et al., *Annu. Rev. Biophys. Biogen.*, 9:467–508 (1980); Deamer and Uster, "Liposomes" Ch. 1, Liposome Preparation: Methods and Mechanisms; Marc J. Ostro (Ed.) M. Dekker, Inc., pp. 27–51 New York, NY (1983); and Szoka, et al., *Proc. Nat'l. Acad. Sci. U.S.A.*, 75:4194–4198 (1978).

Multilamellar vesicles (MLV) are prepared by depositing lipids from organic solvents in a thin film on the wall of a round-bottom flask by rotary evaporation under reduced pressure followed by hydration with aqueous buffers and agitation. Bangham, A., et al., *J. Mol. Biol.*, 13:238–252 (1965). The hydration time, method of resuspension of lipids, and thickness of the lipid film can result in markedly different preparations of MLVs, despite a constant lipid concentration and composition, and volume of suspending aqueous phase. The size ranges obtainable by this method vary from 0.4 to 50 microns (400 to 50,000 nanometers). Papahadjopoulos and Miller, *Biochem. et Biophy. Acta.*, 135:624 (1967). Szoka, F., et al., *Proc. Nat'l. Acad. Sci. U.S.A.*, 75:4194–4198 (1978).

Mezei, et al., U.S. Pat. No. 4,485,054, disclose a procedure for producing large multilamellar lipid vesicles (MLV) which may be used to encapsulate biologically active materials, particularly lipophilic substances. The lipid film forming step is conducted in a vessel partially filled with inert, solid, contact masses, in particular, spherical contact masses having a diameter of 1.0 mm to 100 mm (1,000 to 100,000 microns) and results in liposomes reported to range in diameter from 5 to 10 microns (5,000 to 10,000 nanometers).

MLVs are relatively easy to prepare, can be made from a wide variety of lipid compositions, and are efficiently lysed by complement. Because they have many lamellae, they are stable against leakage and therefore have good shelf life. However, the use of MLVs can be disadvantageous because MLV preparations typically are heterogeneous in size distribution, in shape, and in entrapped volume. For in vivo applications such as drug delivery, the largest MLVs are most readily filtered from the blood stream and consequently most rapidly sequestered in the lungs and reticulo-endothelial system, thereby limiting the circulating half-life of liposome-entrapped drugs and hindering efforts towards tissue specific drug targetting. Scherphof, et al., *Biochem. Soc. Trans.*, 15:345–348 (1987); and Juliano and Stamp, *Bioch. Biophys. Res. Comm.*, 63:651–658 (1975).

When used in complement-mediated assays, the largest MLVs tend to settle, thereby changing the distribution of MLVs in solution and causing a shift in the immunoassay standard curve. Further, liposome lysis varies as a function of both the size and the type of liposome used in the immunoassay. Richards, et al., *Biochem. et Biophys. Acta.*, 855:223–230 (1986). Liposome interaction with plasma also varies as a function of the size and type of liposome. Scherphof, et al., *Liposome Technology*, Volume III, pp. 205–224 Edited by G. Gregnodia, CRC Press Boca Raton, Florida (1984). These results indicate that liposome size is an important parameter which needs to be controlled in order to obtain reproducible complement mediated lysis.

Although the heterogeneous size problem can be overcome by sizing by passage through filters, the filters tend to clog when high concentrations of lipid and large volumes of liposomes are filtered. Clogging is also a function of the lipid composition, e.g., the charge of the lipids used to prepare the liposomes, the interaction with the filter material, and the tendency of the liposomes to aggregate during and after filtration. Frequent changes of filters is both difficult and inconvenient. Generally, filtration is more suitable for research scale preparations rather than production scale preparations. Furthermore, a high lipid concentration is necessary for efficient drug encapsulation if liposomes are to be used for drug delivery.

Despite substantial research and development in methods for producing liposome (especially MLV) preparations for immunoassay and drug delivery use, there continues to exist a need in the art for new, rapid and simple preparatives techniques which are: (1) applicable to liposome formation using widely varying lipid components and concentrations of the same; (2) applicable liposome entrapment of aqueous compositions of widely varying chemical compositions; (3) capable of providing storage stable, substantially homogeneous populations of small sized lipsomes without resort to cumbersome "screening" processes; and (4) susceptible to use in both small and large scale liposome production procedures.

BRIEF SUMMARY OF THE INVENTION

The present invention provides novel methods for generating substantially homogeneously-sized populations of aqueous liquid-encapsulating multilamellar lipid vesicles (liposomes) within mean diameter sizes within the range of from 150 to 3,000 nanometers. In brief, one or more lipids, or lipid conjugates, are suspended in an organic solvent and dried to a thin film on the walls of a vessel. An aqueous liquid to be encapsulated and a collection of spherical contact masses, having a mean diameter of less than 3,000 microns, preferably less than 1,000 microns, and most preferably from 50–100 microns, are then added to the vessel and the vessel is agitated to suspend the lipid film to form a substantially homogeneous population of vesicles having diameters in the range of about 150 to about 3,000 nanometers and preferably less than 1,000 nanometers.

Presently preferred methods provide for liposomes which may be made from a variety of lipids and lipid conjugates, synthetic surfactants, alone or in combination, with or without membrane stabilizers such as cholesterol, and/or charge modifiers, such as phosphatidic acid, and anti-oxidants such as α-tocopherol, and the like, over a broad range of lipid concentrations, including the use of small to moderate amounts of lipid(s) and of marker substances, such as colorimetric or fluorescent dyes, enzymes, or drugs. Both smaller preparations, 1-50 ml, and larger batch preparations, greater than 1 liter, can be prepared by using the appropriate vessel size and agitation apparatus and the process is reproducible from preparation to preparation.

These methods allow for the use of small quantities of marker and lipid, leave no residual solvents, can involve contact only with glass surfaces, and involve no transfer of liposome preparations from lipid film drying vessels to sizing apparatus. The processes require minimal user attention and the liposomes are not contaminated or damaged during the processes. In addition, the techniques permit control of the liposome size ranges, yield liposomes with efficient encapsulation of marker or drug, and yield liposomes which reproducibly lyse with complement reagent in complement-mediated immunoassays. The liposome size ranges obtainable are a function of both the agitation time and the size range of beads used. Generally, within the upper limit of use of less than 1,000 micron diameter beads, use of smaller beads for shorter periods of time results in a similarly sized liposome populations as are obtained using larger beads for longer time periods.

In another of its aspects, the invention provides for a dispersion of substantially non-aggregated multilamellar aqueous liquid-encapsulating lipid vesicles having a mean size distribution ranging from about 150 nanometer to about 3,000 nanometers with presently preferred dispersions of vesicles having a first immunologically active binding pair member (e.g., an antigen) associated with their surfaces and are susceptible to at least 60 percent lysis by excess serum complement in the presence of a stoichiometric amount of a second immunologically active binding pair member (e.g., an antibody).

Other aspects and advantages of the present invention will be apparent upon consideration of the following detailed description thereof which includes numerous illustrative examples of practice of the invention.

DESCRIPTION OF DRAWING

FIG. 1 is a plot of particle mean diameter as a function of time, for liposomes vortexed with different sized glass beads.

DETAILED DESCRIPTION

The present invention provides methods for the preparation of uniformly sized populations of marker or drug encapsulating liposomes. The following examples illustrate practice of the invention. Example 1 relates to a side-by-side comparison of liposome sizes obtained as a function of the size beads used during preparation and as a function of vortexing time. Example 2 relates to the preparation of vortexed liposomes using a digoxigenin conjugate lipid and entrapping a fluorescent marker. Example 3 relates to the preparation of vortexed liposomes using a digoxigenin conjugate lipid and entrapping an enzyme. Example 4 relates to the preparation of vortexed liposomes entrapping a drug. Example 5 relates to the use of vortexed liposomes in an immunoassay.

The examples which follow are for illustrative purposes and are not intended in any way to limit the scope of the invention.

EXAMPLE 1

Variation in Liposome Size as a Function of Vortexing with Different Sized Glass Beads A chloroform/methanol (1:1) solution containing egg sphingomyelin (67.5 micromoles), cholesterol (67.5 micromoles) and stearic acid (15 micromoles) was dried to a thin film on the walls of a 50 mL pear-shaped flask by rotary evaporation. Residual solvent was removed under 40 milli-torr vacuum overnight. To the thin film was added 7.5 mL of buffer containing 100 mM NaCl and 50 mM HEPES at pH 7.0. Eighty 3.0 millimeter (3,000 microns) diameter glass beads were added to the flask and the flask was rotated 10 minutes to suspend the lipid film.

Aliquots of these MLVs from the 50 mL flask were transferred to 5.0 mL pear-shaped flasks and vortexed with small glass beads (ranging in diameter from 3,000 to 50 microns in diameter) as follows. To each flask was added 0.5 mL of MLV suspension and 0.67 gms of a pre-selected size range of glass beads, i.e., 3000; 758; 402; 150–210; and 50–100 microns, respectively, in diameter. The flasks were stopped with glass plugs wrapped with Teflon TM tape and held in place with Parafilm TM. Triplicate samples were run for the 3000 microns and 50–100 micron diameter glass beads; for other size ranges single samples were run. A no-beads control was also run. The 5.0 mL pear-shaped flasks were clamped to the platform of a GLAS-COL(VB-3) vortexer equipped with a plexiglas adapter designed to hold the flasks firmly by the neck. The samples were vortexed (approximately 3 millimeter excursion) side-by-side at 2000 rpm as measured by a digital tachometer.

FIG. 1 shows the changes in the particle mean diameter, as a function of time, for liposomes vortexed with different sized glass beads. Mean diameter was measured by quasi-elastic laser light scattering as calculated by the method of cumulants using a NICOMP Model 200. In the absence of glass beads, vortexing resulted in only a small decrease in mean diameter. The addition of 3000 micron diameter glass beads resulted in smaller diameter liposomes, probably the result of breaking up of the largest particles and aggregates. The use of smaller glass beads, resulted in progressively smaller liposome mean diameters as a function of both vortexing time and glass bead diameter. The triplicate samples prepared using 50-100 micron diameter glass beads showed smaller variance in liposome mean diameter as compared to liposomes prepared using 3000 micron diameter glass beads. The error bars in FIG. 1 are plus and minus the standard deviation.

Most of the changes in mean diameter occurred during the first ten minutes of vortexing. When sized populations of large and small liposomes were mixed together in defined proportions, a weighting in favor of the larger particle diameters has been found in analysis by the method of cumulants (Wong, et al., *Biochemistry*, 21:4133–4139 (1982). The mean diameter in FIG. 1 is conservatively interpreted as an upper limit of liposome diameter. The results in FIG. 1 are also a function of the size of the vortexing flask, the concentration of lipid, the number of glass beads and the vortexing speed. The selection of the appropriate size of the flask, the concentration of lipid, the number of glass beads, the vortexing speed, and the vortexing time may vary as a function of the intended use of the liposomes, but will be apparent to a person skilled in the art. The selection of these parameters will be aided by monitoring liposome size distribution, or by monitoring the reproducibility of results obtained in an immunoassay using vortexed liposomes.

EXAMPLE 2

Preparation of Vortexed Liposomes Containing a Digoxigenin Conjugate and Entrapping a Fluorescent Marker Lipid films containing 20, 40, and 100 micromoles of an egg sphingomyelin (47.25%), cholesterol (47.25%), stearic acid (5.0%) and dipalmitoylphosphatidylethanolamine-digoxigenin (0.5%) mixture were prepared on the walls of 10.0 mL pear-shaped flasks, in triplicate, and dried overnight. To each flask was added 2.4 gms of 50-100 micron diameter glass beads and 2.0 mL solution containing 78 mM tris-amide carboxyfluorescein, 50 mM maltose, 0.02% thimerosal and 5mM HEPES, at pH 7.0. The flasks were stoppered, then vortexed side-by-side at 2100 rpm. Samples were removed at 5, 10, and 45 minutes, respectively. The liposomes were aspirated away from the settled glass beads. Buffer was added to wash the beads twice to recover all the liposomes. Any non-encapsulated free fluorophore was removed from the liposome preparation by washing with 9.0 mL of a solution containing 88 mM NaCl, 50 mM maltose, 0.02% thimerosal and 50 mM HEPES at pH 7.0. The liposome preparation was pelleted at 48,000 g for 45 minutes and the supernatant removed. The liposomes were resuspended and the washing procedure repeated a total of 3 times.

Table 1 shows the changes in liposome signal-to-noise, mean diameter, trapped volume, and % capture as a function of lipid concentration and vortexing time.

TABLE 1

CHARACTERIZATION OF VORTEXED LIPOSOMES PREPARED WITH FLUOROPHORE

| | Lipid Concentration (mM) | Vortex Time (Min) | Signal -to- Noise[1] | Mean Diameter (nM) | Trapped Volume (L/Mole) | % Capture |
|---|---|---|---|---|---|---|
| 1. | 10 | 5 | 25 | 1844 | 12.5 | 11.2 |
| 2. | 10 | 10 | 28 | 1458 | 13.4 | 11.1 |
| 3. | 10 | 45 | 35 | 666 | 20.9 | 16.1 |
| 4. | 20 | 5 | 31 | 2342 | 10.4 | 18.1 |
| 5. | 20 | 10 | 29 | 1648 | 11.3 | 22.3 |
| 6. | 20 | 45 | 52 | 561 | 18.7 | 27.9 |
| 7. | 50 | 5 | 39 | 2513 | 11.2 | 53.6 |
| 8. | 50 | 10 | 40 | 1947 | 11.2 | 53.2 |
| 9. | 50 | 45 | 50 | 922 | 11.6 | 47.9 |

[1]Signal plus noise was measured in the presence of octylglucoside detergent and noise was measured in the absence of octylglucoside. Correction was made for background fluorescence from the detergent and buffer.

As was the case with preparations described in Example 1, mean diameter decreased as a function of vortexing time. Signal-to-noise, trapped volume and % capture increased as a function of vortexing time. The trapped volume decreased and the % capture increased at higher lipid concentrations. The trapped volumes measured for vortexed liposomes prepared with 50-100 micron glass beads (10.4-20.9 liters/mole) were higher than reported by Deamer D. and Uster P (Deamer, et al., "Lipsomes" Ch. 1, Liposome Preparation: Methods and Mechanisms; Marc J. Ostro (Ed.) M. Dekker, Inc., pg. 27-51 New York, New York (1983)) for multilamellar liposomes (2-7 liters/mole). The high % capture at higher lipid concentrations, together with the decreasing mean diameter at longer vortexing times, is an advantage in potential drug delivery applications.

EXAMPLE 3

Entrapping an Enzyme in Liposomes Vortexed with 50-100 micron Diameter Glass Beads A ten micromole lipid film (4.725 micromoles egg sphingomyelin, 4.725 micromoles cholesterol, 0.5 micromole stearic acid, 0.05 micromoles dipalmitoylphosphatidylethanolamine-digoxigenin) was dried on the walls of a 5.0 mL pear-shaped flask.

To the flask were added 0.5 mL of a 20 mg/mL solution of alkaline phosphatase (33,400 Units) in buffer containing 100 mM NaCl, 50 mM trehalose, 1 mM MgCl$_2$, 0.1 mM ZnCl$_2$, 50 mM HEPES at pH 8.0 and 0.6 gms of 50-100 micron diameter glass beads. The flask was vortexed at 2000 rpm for 50 minutes. Unencapsulated free alkaline phosphatase was removed by centrifuging the liposomes at 45,000 g for 30 minutes and removing the supernatant. The liposomes were resuspended in a buffer containing 100 mM NaCl, 50 mM trehalose, 6 mM MgCl$_2$, 1 mM CaCl$_2$, 50 mM HEPES at pH 8.0. The wash step was repeated a total of 4 times.

The ratio of enzyme activity encapsulated versus free enzyme, i.e., unencapsulated, was determined by lysing an aliquot of liposomes with octylglucoside detergent. Reaction rates were measured at 37° C. in the presence of 6 mM p-nitrophenylphosphate substrate. The signal-to-noise was 49.8 and the percent of enzyme encapsulated (measured as enzyme activity) in the liposomes was 98%.

EXAMPLE 4

Entrapping a Drug in Liposomes Vortexed With 50-100 Micron Diameter Beads

A 120 micromole lipid film (54 micromoles egg sphingomyelin, 54 micromoles cholesterol, 12 micromoles stearic acid) was dried on the walls of a 10 mL pear-shaped flask. To the flask was added 6.0 mL of the drug urokinase dissolved in 0.9% saline (120,000 IU/mL) and 3 gms of 50-100 micron diameter glass beads. The flask was stoppered and vortexed for 60 minutes at 2000 rpm. The mean diameter of the liposome suspension was 1509 nanomerers. External urokinase was removed by pelleting the liposomes by centrifugation and resuspending the liposomes in buffer.

EXAMPLE 5

Use of Vortexed Liposomes In an Immunoassay

Digoxigenin-liposomes for use in an immunoassay to detect digoxin were prepared by vortexing a 10 micromole lipid film, having the same composition and fluorophore as described in Example 2, with 50-100 micron diameter glass beads for 45 minutes. The digoxigenin conjugated liposomes comprise the first immunological binding pair member and the digoxin to be assayed comprises the second immunological binding pair member. Rabbit anti-digoxin anti-sera was diluted in the buffer of Example 2 plus 288 mM $MgCl_2$ so as to give 35% of the maximum liposome lysis obtained with 10% octyl glucoside with the 0.0 ng/mL standard. The complement source was seventy percent horse plasma in buffer and the standards included DIGOXIN II FPIA calibrators 9611-01 lot #06998 A2, Abbott Labs, North Chicago.

The assay protocol consisted of the following the indicated time intervals, at 37° C.: (i) add 25 microliters sample to 45 microliters 0.1 N HCl and incubate for 30 seconds; then add buffer to give a final sample dilution of 1:88; (ii) add 45 microliters antisera to 365 microliters sample, diluted 1:88, and incubate for 5 minutes; (iii) add 500 microliters buffer containing 625 picomoles liposomes and incubate for 10 minutes; (iv) add 60 microliters complement to 60 microliters of the incubate of step (iii) and incubate for 10 minutes; dilute this mixture 1:13 with buffer; and (v) read the fluorescence intensity at excitation: 490 nm and emission: 520 nm.

Table 2 shows a digoxin standard curve generated using vortexed liposomes, on an automated instrument programmed to perform the reagent additions and to read fluorescence. These results indicate an inverse relationship of the fluorescence intensity and the amount of digoxin in the sample.

TABLE 2

DIGOXIN STANDARD CURVE

| Calibrator Standard (ng/mL) | Fluorescence Intensity | Mean | CV (S.D/Mean) (%) |
|---|---|---|---|
| 0.0 | 4838 | | |
| | 4963 | | |
| | 4882 | | |
| | 4819 | 4876 | 1.14 |
| 0.5 | 4490 | | |
| | 4256 | | |
| | 4235 | | |
| | 4278 | 4315 | 2.38 |
| 1.0 | 3898 | | |
| | 4025 | | |
| | 3983 | 3969 | 1.34 |
| 2.0 | 3288 | | |
| | 3301 | | |
| | 3259 | 3283 | 0.54 |
| 3.0 | 2744 | | |
| | 2677 | | |
| | 2856 | 2759 | 2.68 |
| 5.0 | 1645 | | |
| | 1616 | | |
| | 1675 | 1645 | 1.47 |

The foregoing illustrative examples relate to the preparation of sized populations of liposomes. While the present invention has been described in terms of specific methods and compositions, it is understood that variations and modifications will occur to those skilled in the art upon consideration of the present invention.

For example, it is envisioned that mixtures of large and small diameter vortexing spheres, such as greater than and less than 1,000 microns in diameter, may be equally effective. Also, while the use of glass beads has been described, it will apparent that other non-glass vortexing spheres, such as metal or ceramic or the like, may be employed in the practice of the invention. Moreover, while specific vortexing times and speeds have been described, the use of other vortexing times and speeds may readily be used according to the invention. The use of various other glass and non-glass vortexing vessels of other shapes and volumes, other than those flasks specifically described, may be equally effective.

Similarly, while lipid films have been described comprised of sphingomyelin, cholesterol, stearic acid, and dipalmitoylphosphatidylethanolaminedigoxigenin, other lipids and lipid conjugates such as phosphatidylcholine, phosphatidylethanolamine, various glycolipids, single-chain lipids, fatty acids, dialkyltype synthetic surfactants, and the like may be used alone or in combination. These components may contain membrane stabilizers in addition to cholesterol, such as cholestanol and the like and/or charge modifiers, such as phosphatidic acid, dicetylphosphate, stearylamine, and anti-oxidants such as alpha-tocopherol, over a broad range of concentrations.

In addition, other enzymes can be encapsulated other than urokinase, such as alkaline phosphatase, $\beta$-galactosidase, and $\beta$-lactamase. Other fluorophores, such as calcein, carboxyfluorescein, n-methyl glucamide carboxyfluorescein, and chromophores such as sulforhodamine B may also readily be used. Similarly chemiluminescent markers, radioisotopes, contrast agents, paramagnetic or NMR detectable agents can be incorporated.

Numerous modifications and variations in the invention as described in the above illustrative examples are expected to occur to those skilled in the art and consequently only such limitations as appear in the appended claims should be placed thereon. Accordingly, it is intended in the appended claims to cover all such equivalent variations which come within the scope of the invention as claimed.

What is claimed is:

1. A dispersion of substantially homogeneously sized multilamellar lipid vesicles having means vesicle diameters within the range of from about 150 to about 3000 nanometers, said dispersion being prepared by:
    (1) adding to a vessel one or more lipids in an organic solvent, said organic solvent being in an amount which allows said lipids to be dried as a film on the walls of said vessel;
    (2) drying said lipids to a thin film onto the walls of said vessel;
    (3) adding to said vessel an aqueous liquid and a collection of contact masses having mean diameters within the range of from about 50 to about 3,000 microns, said aqueous liquid being in an amount sufficient to result in a concentration of lipid which is less than about 1 mole per liter of said lipid in said aqueous liquid, and said contact masses being in an amount which is not: (a) so numerous that agitation of said masses in said vessel cannot be performed; and (b) so small that collisions between said contact masses and collisions between said contact masses and said walls cannot occur; and
    (4) agitating said vessel to form said dispersion of substantially homogeneously sized multilamellar vesicles.

2. The dispersion of liquid vesicles according to claim 1, wherein said vesicles have a first immunological binding pair member associated with their surfaces and are susceptible to at least 60% lysis by excess serum complement in the presence a stoichiometric amount of a second immunological binding pair member.

3. The dispersion of lipid vesicles according to claim 2, wherein said first immunological binding pair member is phophatidylethanolamine-digoxigenin.

* * * * *